(12) United States Patent
Prevrhal et al.

(10) Patent No.: US 9,638,812 B2
(45) Date of Patent: May 2, 2017

(54) RECONSTRUCTION APPARATUS FOR RECONSTRUCTING A PET IMAGE

(71) Applicant: KONINKLIJKE PHILIPS N.V., Eindhoven (NL)

(72) Inventors: Sven Prevrhal, Hamburg (DE); Michael Grass, Buchholz in der Nordheide (DE); Eberhard Sebastian Hansis, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/100,648

(22) PCT Filed: Nov. 24, 2014

(86) PCT No.: PCT/EP2014/075391
§ 371 (c)(1),
(2) Date: Jun. 1, 2016

(87) PCT Pub. No.: WO2015/082243
PCT Pub. Date: Jun. 11, 2015

(65) Prior Publication Data
US 2016/0306054 A1 Oct. 20, 2016

(30) Foreign Application Priority Data
Dec. 4, 2013 (EP) ...................... 13195711

(51) Int. Cl.
*G01T 1/164* (2006.01)
*G01T 1/29* (2006.01)
(Continued)

(52) U.S. Cl.
CPC ............ *G01T 1/2985* (2013.01); *A61B 6/037* (2013.01); *G01T 1/161* (2013.01)

(58) Field of Classification Search
CPC ......... G06T 2207/10104; G01T 1/2985; G01T 1/172
See application file for complete search history.

(56) References Cited

U.S. PATENT DOCUMENTS

| | | | |
|---|---|---|---|
| 6,294,788 B1 * | 9/2001 | Cooke | ..................... G01T 1/172 250/363.03 |
| 2003/0036700 A1 | 2/2003 | Weinberg | |

(Continued)

FOREIGN PATENT DOCUMENTS

| | | |
|---|---|---|
| WO | 01/01167 | 1/2001 |
| WO | 2007/054843 | 5/2007 |

(Continued)

OTHER PUBLICATIONS

Schnall, et al., "Prostate: MR imaging with an endorectal surface coil", Radiology, 172(2), 570-574 (1989).

(Continued)

*Primary Examiner* — Kiho Kim (57) ABSTRACT

A reconstruction apparatus (9) reconstructs a PET image. A first detector (3) generates first detection events and detection times assigned to the first detection events and a second detector (6) generates second detection events and detection times assigned to the second detection events. A timing window determination unit (11) provides a first-second timing window by providing a first-second upper threshold based on the position of the second detector relative to the first detector and a detection event pairs generation unit (12) generates first-second detection event pairs based on the provided first-second timing window. The first-second detection event pairs are used for reconstructing the PET image. The first-second timing window depends on the position of the second detector leads to an improved gen- (Continued)

eration of first-second detection event pairs, which in turn can lead to an improved PET image.

16 Claims, 4 Drawing Sheets

(51) Int. Cl.
G01T 1/161 (2006.01)
A61B 6/03 (2006.01)

(56) References Cited

U.S. PATENT DOCUMENTS

2004/0054248 A1 3/2004 Kimchy
2005/0055174 A1 3/2005 David
2007/0106154 A1 5/2007 Conti
2010/0187424 A1 7/2010 Majewski

FOREIGN PATENT DOCUMENTS

WO 2007/082126 7/2007
WO 2012/069960 5/2012
WO 2012/171009 12/2012
WO 2013/050941 4/2013

OTHER PUBLICATIONS

Garutti, et al., "Single channel optimization for an endoscopic time-of-flight positron emission tomography detector", IEEE Nuclear Science Symposium, Medical Imaging Conference, 54 (2011).

Synder, et al., "Image Reconstruction from List-Mode Data in an Emission Tomography System Having Time-of-Flight Measurements", IEEE Transactions on Nuclear Science, 30:1843-1849 (1983).

* cited by examiner

RECONSTRUCTION APPARATUS FOR RECONSTRUCTING A PET IMAGE

CROSS REFERENCE TO RELATED APPLICATIONS

This application is the U.S. National Phase application under 35 U.S.C. §371 of International Application No. PCT/EP2014/075391, filed Nov. 24, 2014, published as WO 2015/082243 on Jun. 11, 2015, which claims the benefit of European Patent Application Number 13195711.0 filed Dec. 4, 2013. These applications are hereby incorporated by reference herein.

FIELD OF THE INVENTION

The invention relates to a reconstruction apparatus, a reconstruction method and a reconstruction computer program for reconstructing a positron emission tomography (PET) image. The invention relates further to a PET system comprising the reconstruction apparatus and a corresponding PET method and PET computer program.

BACKGROUND OF THE INVENTION

US 2003/0036700 A1 discloses a system for obtaining an image of a body part within a body, wherein a radiotracer including Indium-III has been administered intravenously to the body such that the radiotracer accumulates preferentially in the body part. The system comprises a first gamma ray sensor configured to detect prompt gamma rays emitted by Indium-III, wherein the first gamma ray sensor is positioned external to the body, and a second gamma ray sensor configured to detect prompt gamma rays emitted by Indium-III, wherein the second gamma ray sensor is positioned either internally within the body or within a body orifice or body cavity.

WO 2007/082126 A2 discloses a time-of-flight imaging apparatus, wherein the apparatus comprises a) a window generator that generates a dynamic acceptance window based on a profile of a subject and an intrinsic resolution of the imaging system, b) a plurality of radiation detectors that generate signals indicative of each radiation event detection, and c) a line of response processor that identifies a spatial line of response connecting a pair of radiation detections corresponding to a common radiation event. The apparatus further comprises d) a windowing component that filters the radiation event detections by using the dynamic acceptance window and e) a reconstruction engine that reconstructs images based on the remaining non-filtered radiation event detections.

A PET system may comprise an outer detector ring and a PET endoprobe to be introduced into a person. The outer detector ring and the PET endoprobe are adapted to detect gamma ray photons generated within the person, when corresponding radioisotopes decay by positron emission. When a positron is emitted by a nucleus, it almost instantly finds an electron, and the pair annihilates, converting all the mass energy of the two particles into gamma ray photons travelling in opposite directions. A substantially simultaneous detection of these gamma ray photons in two detector elements places the radiation source, i.e. the radioisotopes, on a line connecting the two detector elements, wherein two gamma ray photons are regarded as being simultaneously detected, if a difference between the respective detection times is smaller than a preset threshold. A lot of different coincident gamma ray photons and thus corresponding lines, on which the radiation source is arranged, are detected, wherein these lines can be used for reconstructing a PET image. However, the quality of the PET image may be relatively low in comparison to, for instance, a magnetic resonance (MR) image or a computed tomography (CT) image.

SUMMARY OF THE INVENTION

It is an object of the present invention to provide a reconstruction apparatus, a reconstruction method and a reconstruction computer program for reconstructing a PET image having an improved quality. It is a further object of the present invention to provide a PET system comprising the reconstruction apparatus and a corresponding PET method and PET computer program.

In a first aspect of the present invention a reconstruction apparatus for reconstructing a PET image of an object is presented, the reconstruction apparatus being adapted to reconstruct the PET image based on detection events and detection times assigned to the detection events generated by a PET data acquisition apparatus of a PET system, wherein the PET data acquisition apparatus comprises:

a first detector with first detector elements for detecting photons emitted by a radiation source located within the object and for generating first detection events being indicative of the detected photons and detection times assigned to the first detection events, a second detector with second detector elements for detecting photons emitted by the radiation source and for generating second detection events being indicative of the detected photons and detection times assigned to the second detection events, wherein the reconstruction apparatus comprises:

a position providing unit for providing the position of the second detector relative to the first detector, a timing window determination unit for providing a first-second timing window by providing a first-second upper threshold, wherein the first-second timing window is provided based on the position of the second detector relative to the first detector, a detection event pairs generation unit for generating first-second detection event pairs based on the provided first-second timing window, wherein a first-second detection event pair comprises a first detection event and a second detection event, to which detection times have been assigned whose difference is equal to or smaller than the first-second upper threshold, and a reconstruction unit for reconstructing the PET image based on the generated first-second detection event pairs.

Since the position of the second detector, i.e. the location and orientation of the second detector, relative to the first detector is provided and since the first-second timing window is provided based on the provided position of the second detector, the first-second timing window can be tailored to the current position of the second detector. For instance, the first-second timing window can be tailored such that differences between detection times assigned to a second detection event and a first detection event, which correspond to photons caused by the same decay event, which are maximally possible in view of the current spatial relation between the corresponding first and second detector elements, are within the first-second timing window. This improved tailoring of the first-second timing window can lead to an improved generation of first-second detection event pairs, which in turn can lead to an improved PET image.

The first detector is preferentially an outer detector, which is adapted to be used outside of the object, and the first detector elements are preferentially outer detector elements. The second detector is preferentially an inner detector, which is adapted to be used within the object. In an embodiment the outer detector is an outer detector ring surrounding an examination region and the second detector is an inner detector within the examination region, wherein the inner detector can be adapted to be arranged within the object or outside of the object.

In an embodiment the timing window determination unit is adapted to provide the first-second timing window by further providing a first-second lower threshold, wherein a first-second detection event pair comprises a second detection event and a first detection event, to which detection times have been assigned whose difference is equal to or smaller than the first-second upper threshold and equal to or larger than the first-second lower threshold. Generating the detection event pairs also based on lower thresholds can further improve the accuracy of generating these pairs and finally lead to a further improved quality of the PET image.

The reconstruction apparatus may further comprise a region of interest providing unit for providing a region of interest within the object which should be shown by the PET image, wherein the timing window determination unit can be adapted to determine the first-second timing window based on the provided region of interest. In particular, the region of interest may be regarded as defining the region, in which the photon pairs can be simultaneously generated, wherein this knowledge about the extension of the possible emission region can be used for tailoring the first-second timing window accordingly. This can further improve the accuracy of generating the detection event pairs and finally lead to a further improved quality of the PET image.

The provided position of the second detector defines the positions of the second detector elements relative to the first detector elements, wherein the timing window determination unit can be adapted to provide a respective first-second timing window depending on a position of a respective first detector element relative to a position of a respective second detector element, which have been used for generating a respective first detection event and a respective second detection event, wherein the detection event pairs generation unit can be adapted to use the respective first-second timing window for determining whether the respective first detection event and the respective second detection event form a first-second detection event pair. Thus, the first-second timing window may be adapted to the respective pair of detector elements, thereby allowing for a further improved tailoring of the first-second timing window, which in turn may lead to a further improved quality of the finally reconstructed PET image.

The timing window determination unit may be adapted to provide a respective first-second upper threshold depending on a distance between the position of the respective first detector element and the position of the respective second detector element. Moreover, the timing window determination unit may be adapted to provide a respective first-second timing window based on the borders of a provided region of interest along a line connecting the respective second detector element and the respective first detector element. Also this can lead to a further improved tailoring of the first-second timing window and, thus, finally to a PET image having a further improved image quality.

In a preferred embodiment the position providing unit is adapted to provide the position of the second detector relative to the first detector based on an image, which is generated by a further imaging system like an MR or CT system integrated with the PET system and which shows the second detector, and based on a known spatial relation between the first detector and the further imaging system, which may be known, for instance, from a previous calibration step. In a further embodiment the position providing unit is adapted to provide the position of the second detector relative to the first detector based on photons, which have been emitted by PET markers of the second detector and which have been detected by the first detector. These techniques allow determining the position of the second detector very accurately, which in turn allows for a very accurate tailoring of the first-second timing window and thus to a further improved quality of the PET image.

Preferentially, the timing window determination unit is further adapted to provide a first-first timing window by providing a first-first upper threshold, wherein the detection event pairs generation unit is adapted to generate first-first detection event pairs based on the provided first-first timing window, wherein a first-first detection event pair comprises first detection events, to which detection times have been assigned whose difference is equal to or smaller than the first-first upper threshold, and the reconstruction unit is adapted to reconstruct the PET image based on the generated first-second detection event pairs and first-first detection event pairs. Moreover, the timing window determination unit may be adapted to provide the first-first timing window by further providing a first-first lower threshold, wherein a first-first detection event pair comprises first detection events to which detection times have been assigned whose difference is equal to or smaller than the first-first upper threshold and equal to or larger than the first-first lower threshold. Furthermore, the timing window determination unit may be adapted to determine the first-first timing window based on the provided region of interest. In an embodiment the timing window determination unit is adapted to provide a respective first-first timing window depending on a position of a respective first detector element and a position of a respective further first detector element, which have been used for generating a respective first detection event and a respective further first detection event, wherein the detection event pairs generation unit is adapted to use the respective first-first timing window for determining whether the respective first detection event and the respective further first detection event form a first-first detection event pair. In particular, the timing window determination unit can be adapted to provide a respective first-first timing window based on the borders of the region of interest along a line connecting the respective first detector element and the respective further first detector element. This can lead to a tailoring of the first-first timing windows, which can improve the generation of first-first detection event pairs and thus of the final PET image.

In another aspect of the present invention a PET system for generating a PET image of an object is presented, wherein the PET system comprises:
  a PET data acquisition apparatus with:
    a first detector with first detector elements for detecting photons emitted by a radiation source located within the object and for generating first detection events being indicative of the detected photons and detection times assigned to the first detection events,
    a second detector with second detector elements for detecting photons emitted by the radiation source and for generating second detection events being indicative of the detected photons and detection times assigned to the second detection events,
a reconstruction apparatus for reconstructing a PET image.

The second detector may be adapted for being introduced into the object for detecting the photons inside the object. In particular, the second detector may be regarded as being a PET endoprobe. In another embodiment the second detector may be adapted for being arranged on an outer surface of the object. If the second detector is arranged at these locations, the photons can be detected by the second detector relatively close to the location where the photons have been generated. This can lead to an improved quality of detecting the photons, because, for instance, the likelihood of being scattered and/or absorbed while traveling from the radioisotopes to the second detector can be reduced.

In another aspect of the present invention a reconstruction method for reconstructing a PET image of an object is presented, the reconstruction method being adapted to reconstruct the PET image based on detection events and detection times assigned to the detection events generated by a PET data acquisition apparatus of a PET system, wherein the PET data acquisition apparatus comprises:
  a first detector with first detector elements for detecting photons emitted by a radiation source located within the object and for generating first detection events being indicative of the detected photons and detection times assigned to the first detection events,
  a second detector with second detector elements for detecting photons emitted by the radiation source and for generating second detection events being indicative of the detected photons and detection times assigned to the second detection events, wherein the reconstruction method comprises:
  providing the position of the second detector relative to the first detector by a position providing unit,
  providing a first-second timing window by providing a first-second upper threshold by a timing window determination unit, wherein the first-second timing window is provided based on the position of the second detector,
  generating first-second detection event pairs based on the provided first-second timing window by a detection event pairs generation unit, wherein a first-second detection event pair comprises a second detection event and a first detection event, to which detection times have been assigned whose difference is equal to or smaller than the first-second upper threshold, and
  reconstructing the PET image based on the generated first-second detection event pairs by a reconstruction unit.

In a further aspect of the present invention a PET method for generating a PET image of an object is presented, wherein the PET method comprises:
  detecting photons emitted by a radiation source located within the object and generating first detection events being indicative of the detected photons and detection times assigned to the first detection events by first detector elements of a first detector,
  detecting photons emitted by the radiation source and generating second detection events being indicative of the detected photons and detection times assigned to the second detection events by second detector elements of a second detector,
  the steps of the reconstruction method for reconstructing a PET image as discussed above.

In another aspect of the present invention a reconstruction computer program for reconstructing a PET image of an object is presented, wherein the computer program comprises program code means for causing a reconstruction apparatus discussed above to carry out the steps of the reconstruction method discussed above, when the computer program is run on a computer controlling the reconstruction apparatus.

In a further aspect of the present invention a PET computer program for generating a PET image of an object is presented, wherein the computer program comprises program code means for causing a PET system to carry out the steps of the PET method as discussed above, when the computer program is run on a computer controlling the PET system.

It shall be understood that a preferred embodiment of the invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
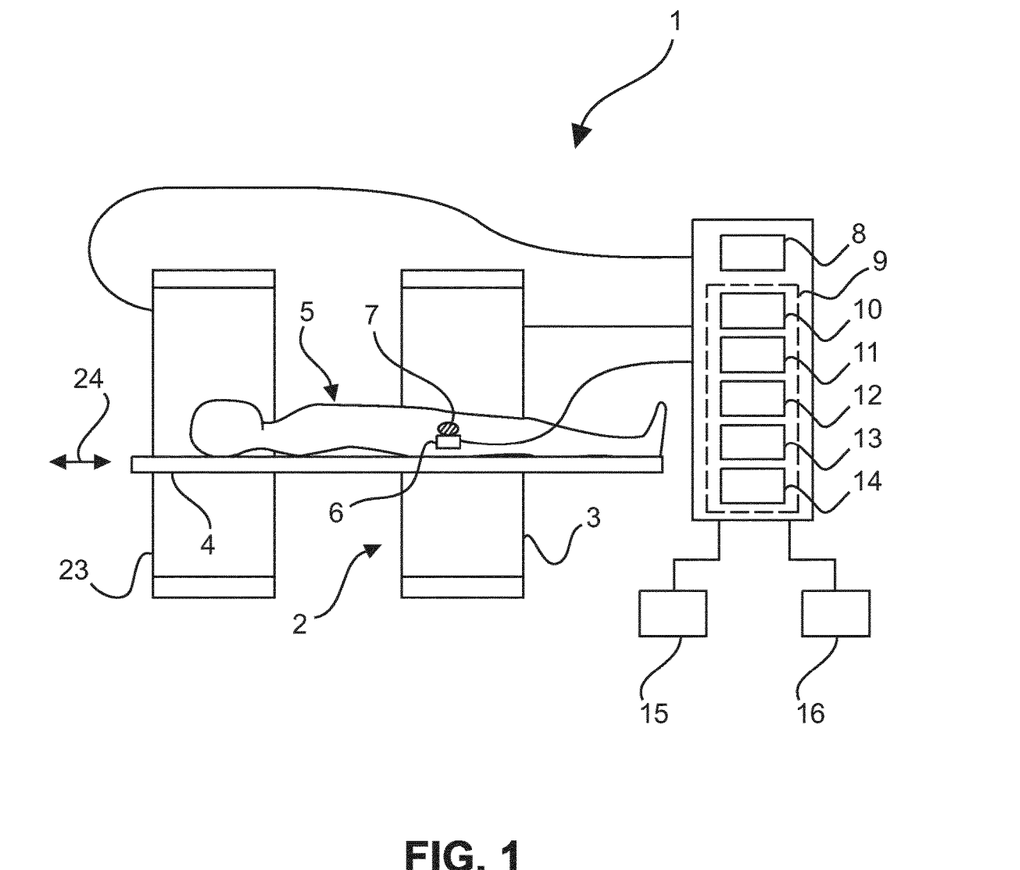
FIG. 1 shows schematically and exemplarily an embodiment of a PET/MR system.

FIG. 1 shows schematically and exemplarily an embodiment of a combined PET/MR system for generating a PET image and an MR image of a person 5 lying on a support means 4 like a table. The PET system 1 comprises a PET data acquisition apparatus 2 including a first detector 3 with first detector elements for detecting photons emitted by a radiation source located within the person 5 and for generating first detection events being indicative of the detected photons and detection times assigned to the first detection events. The PET data acquisition apparatus 2 further comprises a second detector 6 with second detector elements for detecting photons emitted by the radiation source located within the person 5 and for generating second detection events being indicative of the detected photons and detection times assigned to the second detection events. The first and second detectors preferentially comprise solid-state detector elements for detecting the photons.

In this embodiment the first detector 3 is an outer detector ring and the first detector elements 18 are outer detector elements, wherein the outer detector ring 3 surrounds an examination region, and the second detector 6 is an inner detector and the second detector elements 19 are inner detector elements, wherein the inner detector 6 is adapted for detecting the photons inside the outer detector ring 3.

Correspondingly, the first detection events can be regarded as being outer detection events and the second detection events can be regarded as being inner detection events.

The radiation source comprises radionuclides like fluorodeoxyglucose (FDG), carbon-11, nitrogen-13, oxygen-15, et cetera. The radionuclides have been administered, i.e., for instance, injected or orally administered, to the person 5 and gathered at least in a region of interest 7 being, in this embodiment, the prostate of the person 5.

The PET/MR system 1 further comprises a reconstruction apparatus 9 including a position providing unit 10 for providing the position, i.e. the location and orientation, of the inner detector 6 within the person 5 relative to the outer detector ring 3 and a timing window determination unit 11 for providing a first-second timing window based on the position of the inner detector 6 and for providing a first-first timing window. The first-second timing window defines first-second detection event pairs, wherein a first-second detection event pair comprises a second detection event and a first detection event and wherein a difference between the detection times assigned to the second and first detection events is equal to or smaller than an upper threshold of the first-second timing window. The first-first timing window defines first-first detection event pairs, wherein a first-first detection event pair comprises first detection events and wherein a difference between the detection times assigned to the first detection events is equal to or smaller than an upper threshold of the first-first timing window.

Since in this embodiment the first detector 3 is an outer detector ring and the second detector 6 is an inner detector, the first-second timing window can be regarded as being an outer-inner timing window and the first-first timing window can be regarded as being an outer-outer timing window. Correspondingly, the first-second detection event pairs can be regarded as being outer-inner detection event pairs and the first-first detection event pairs can be regarded as being outer-outer detection event pairs.

The reconstruction apparatus 9 further comprises a detection event pairs generation unit 12 for generating outer-inner detection event pairs and outer-outer detection event pairs based on the provided outer-inner timing window and the provided outer-outer timing window and a reconstruction unit 13 for reconstructing the PET image based on the generated outer-inner detection event pairs and outer-outer detection event pairs, i.e. based on the LOCs defined by the respective detection event pairs.

The PET/MR system further comprises an MR data acquisition apparatus 23 for acquiring MR data, which can be used by the reconstruction unit 13 for reconstructing an MR image. The support means 4 is preferentially movable in a longitudinal direction, which is indicated by the double arrow 24 in FIG. 1, such that the region of interest 7 can be moved from the outer PET detector ring 3 to the MR data acquisition apparatus 23 and vice versa, in order acquire PET and MR data and to reconstruct PET and MR images of the region of interest 7. Moreover, in this embodiment the inner detector 6 further comprises a coil for generating MR data, which can also be used by the reconstruction unit 13 for reconstructing the MR image. The MR data acquisition apparatus 23, the outer PET detector ring 3 and the inner detector 6 with the inner PET detector elements and the coil for generating MR data can be configured as disclosed in, for instance the article "Prostate: MR imaging with an endorectal surface coil" by M. D. Schnall et al., Radiology, 172(2), 570-574 (1989), which describes an MR data acquisition apparatus including an endocoil and which is herewith incorporated by reference, and as disclosed in, for instance, "Single channel optimization for an endoscopic time-of-flight positron emission tomography detector" by E. Garutti et al., IEEE Nuclear Science Symposium, Medical Imaging Conference, 54 (2011), which describes a combination of an outer PET detector ring and a PET endoprobe and which is also herewith incorporated by reference. The disclosed endocoil and the disclosed PET endoprobe can be integrated, i.e., for example, put together, for providing a combined PET/MR endoprobe. The PET/MR endoprobe may of course also be constructed in another way. For example, the disclosed PET endoprobe may be equipped with PET detector elements or the PET endoprobe may be equipped with a coil for providing the combined PET/MR endoprobe.

The provided position of the inner detector 6 defines the positions of the inner detector elements relative to the outer detector elements, wherein the timing window determination unit 11 is preferentially adapted to provide a respective outer-inner timing window depending on a position of a respective outer detector element and a position of a respective inner detector element, which have been used for generating a respective outer detection event and a respective inner detection event, wherein the detection event pairs generation unit 12 is preferentially adapted to use the respective outer-inner timing window for determining whether the respective outer detection event and the respective inner detection event form an outer-inner detection event pair. In particular, the timing window determination unit 11 can be adapted to provide a respective outer-inner timing window depending on a distance between the position of the respective outer detector element and the position of the respective inner detector element. In the following this will be illustrated with reference to FIG. 2.

Figure 2:
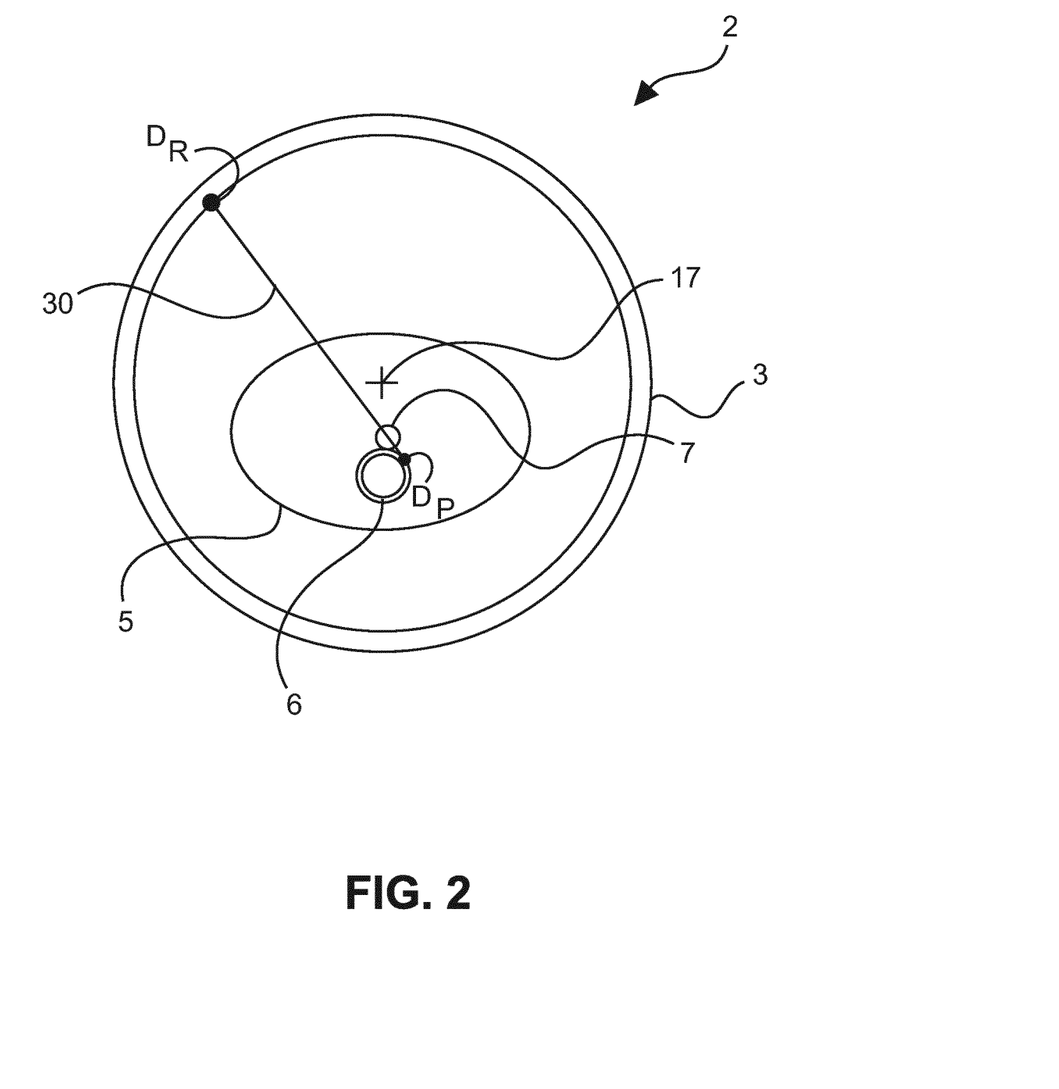
FIG. 2 illustrates schematically and exemplarily a distance between an outer detector element of an outer detector ring and an inner detector element of an inner detector of the PET/MR system,
FIG. 3 schematically and exemplarily illustrates distances along a line of coincidence (LOC) between an outer detector element of the outer detector ring and an inner detector element of the inner detector of the PET/MR system,
FIG. 4 schematically and exemplarily illustrates a reduced time-of-flight (TOF) window.

In FIG. 2 within the region of interest 7 a pair of photons has been generated, which are detected by the outer detector element at the position $D_R$ and by the inner detector element at the position $D_P$, wherein a LOC 30 connects these two detector elements. The upper threshold $\tau_P^U$ of the outer-inner timing window may then be defined by following equation:

$$\tau_P^U = \frac{\overline{D_R D_P}}{c} + \Delta t, \qquad (1)$$

wherein $\overline{D_R D_P}$ denotes the distance between the respective outer detector element and the respective inner detector element, c denotes the speed of light and $\Delta t$ denotes a measurement imprecision, which may be determined by calibration. In FIG. 2 the cross 17 denotes the center of the outer ring detector 3. It should be noted that in FIG. 2 the dots at the positions $D_R$ and $D_P$ are only virtual dots and used only for indicating the respective position.

The outer-inner timing window is tailored to the characteristics of the inner detector 6, i.e. especially to the position of the inner detector 6, wherein the outer-outer timing window is preferentially larger than the outer-inner timing window. Since the position providing unit 10 determines the location and orientation of the inner detector 6, i.e. the location and orientation of the inner detector 6 in a ring coordinate system defined by the outer detector ring 3, the outer-inner timing windows can be individually shaped to each line of coincidence (LOC), also called a line of response, as a function of the distance between the respective outer detector element at the position $D_R$ and the respective inner detector element at the position $D_P$ as described above with reference to equation (1). Also the outer-outer timing window can be individually tailored, i.e. for each ring-ring LOC an individual outer-outer timing window can be provided. In particular, the respective outer-outer timing window may depend on the distance between the respective outer detector elements of the outer detector ring 3 that have detected the respective pair of photons. Also the upper threshold of the outer-outer timing window can be defined as described above in equation (1) with respect to the outer-inner timing window, i.e. also the upper threshold of the outer-outer timing window can be defined as the sum of a) the respective distance between the respective outer detector elements of the outer detector ring divided by the speed of light and b) the measurement imprecision.

The PET/MR system further comprises a region of interest providing unit 14 for providing a region of interest within the person 5 which should be shown by the PET image, wherein the timing window determination unit 11 can be adapted to determine the outer-inner timing window and the outer-outer timing window also based on the provided region of interest. In this embodiment the region of interest is the prostate 7 and the region of interest providing unit 14 is adapted to segment the prostate 7 within the MR image for providing the region of interest.

The respective timing window can be further narrowed such that a random coincidence rejection can be improved by tailoring the respective timing window to the arrival time difference of emission photons from events inside the region of interest 7, which might be regarded as being a predefined region of interest. If the region of interest 7 is considered while providing the timing windows, the respective timing window is preferentially characterized by an upper bound and also by a lower bound that are functions of the eccentricity of the region of interest 7 with respect to the coincident detector elements. This will in the following be explained in more detail with reference to FIG. 3.

Figure 3:
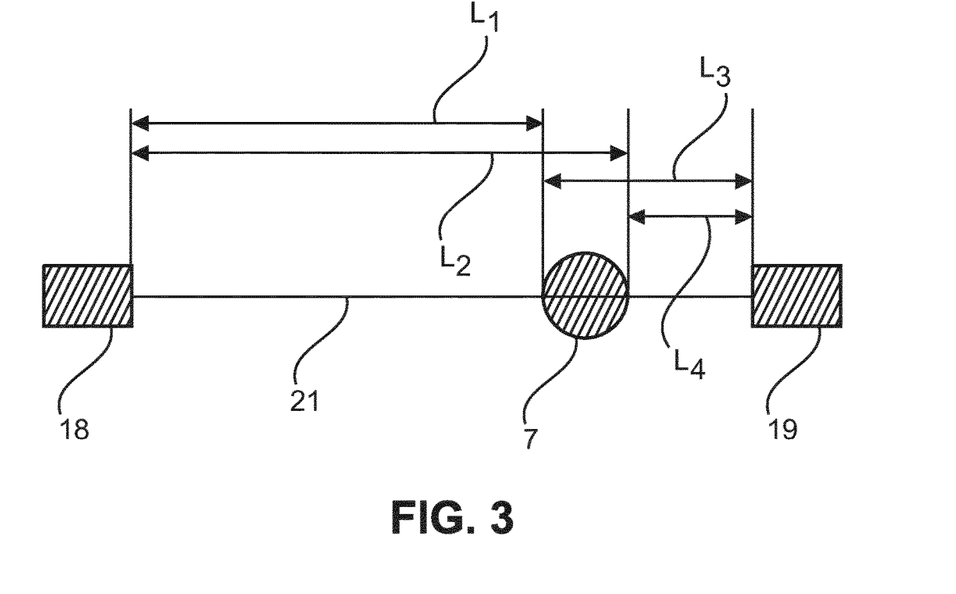

FIG. 3 schematically and exemplarily illustrates an outer detector element 18 and an inner detector element 19, which detect photons generated within the region of interest 7 and traveling along the LOC 21. Maximally and minimally possible differences between the detection times can be defined by following equations:

$$\Delta t_{max} = \frac{L_2 - L_4}{c} \quad (2)$$

and $$\Delta t_{min} = \frac{L_1 - L_3}{c}. \quad (3)$$

In these equations $\Delta t_{max}$ denotes the maximally possible difference between detection times, which are assigned to detection events generated by the outer detector element 18 and the inner detector element 19 and which correspond to a decay event within the region of interest 7, $\Delta t_{min}$ denotes the minimally possible difference between the detection times, which are assigned to detection events generated by the outer detector element 18 and the inner detector element 19 and which correspond to a decay event within the region of interest 7, $L_2$ denotes the maximal distance between the ring detector element 18 and the region of interest 7 along the LOC 21, $L_4$ denotes the minimal distance between the region of interest 7 and the inner detector element 19 along the LOC 21, $L_1$ denotes the minimal distance between the outer detector element 18 and the region of interest 7 along the LOC 21, $L_3$ denotes the maximal distance between the region of interest 7 and the inner detector element 19 along the LOC 21 and c denotes the velocity of the photons. Upper and lower bounds of the outer-inner timing window $\tau_P$, i.e. the outer-inner lower and upper thresholds, can be defined by following equation:

$$\Delta t_{min} - \Delta t \leq \tau_P \leq \Delta t_{max} + \Delta t, \quad (4)$$

wherein $\Delta t$ denotes again the measurement imprecision. Thus, the outer-inner lower and upper thresholds, i.e. the respective outer-inner timing window, can be determined based on the borders of the region of interest 7 along the respective LOC 21 connecting the respective inner detector element 19 and the respective outer detector element 18, i.e. based on the distances between these borders and the respective inner detector element 19 and the respective outer detector element 18. Also the outer-outer timing window may be provided based on the borders of the region of interest along a LOC connecting, in this case, the respective outer detector element and the respective further outer detector element. Thus, also outer-outer lower and upper thresholds can be determined based on minimal and maximal distances between the region of interest 7 and the respective outer detector elements of the outer detector ring 3 similarly to the determination of the outer-inner lower and upper thresholds described above with reference to equations (2) to (4) and FIG. 3.

Figure 4:
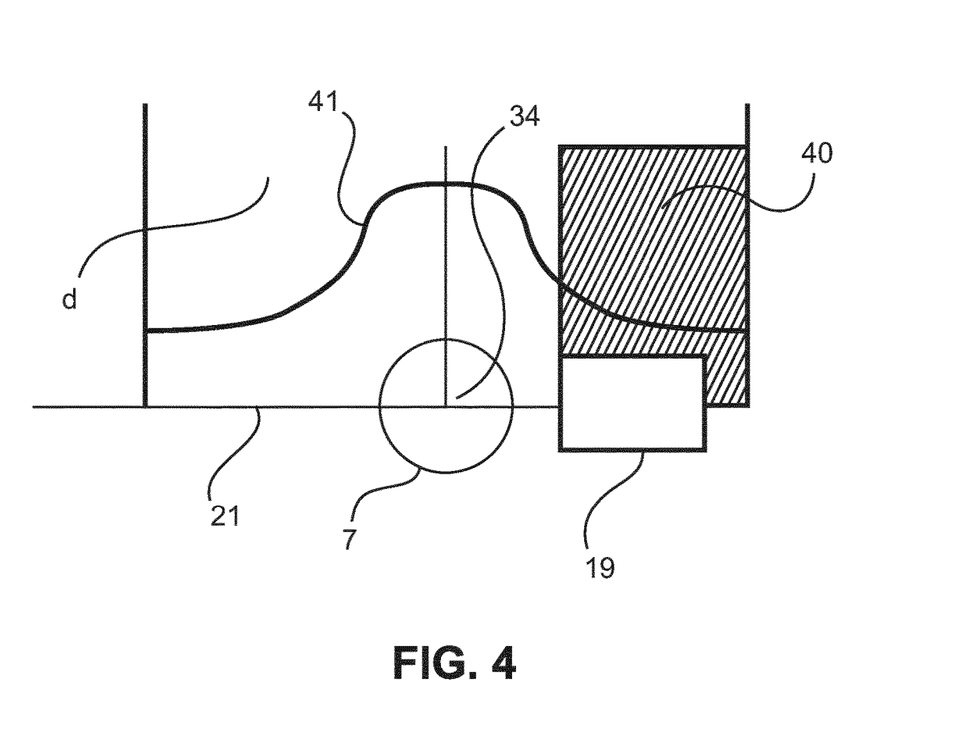

The reconstruction unit 13 can be adapted to reconstruct the PET image based on the generated outer-inner detection event pairs and outer-outer detection event pairs by using known PET reconstruction algorithms, especially by using a TOF reconstruction algorithm. If a TOF reconstruction algorithm is applied to the outer-inner detection event pairs and outer-outer detection event pairs, the assigned detection times are not only used for determining whether detected photons are caused by the same decay event, but the detection times are also used for estimating the position of the decay event along the respective LOC based on differences in the detection times. For instance, if the detection times assigned to detection events of a detection event pair are equal, it can be assumed that the corresponding decay event is likely centrally located on the respective LOC, whereas, if the detection times strongly differ, it can be assumed that the decay event is located on the respective LOC likely closer to one of the detector elements having generated the detection events of the respective pair. During the TOF reconstruction probability functions 41, particularly Gaussian functions, are used for indicating the probability that a decay event is located at a respective location along a LOC 21 as illustrated in FIG. 4. The maximum of the respective probability function 41 is arranged at the location 34 defined by the difference between the detection times of the detection events defining the respective LOC 21. The probability functions 41 are further defined by the positions of the respective inner detector element 19 and the respective outer detector element forming the respective LOC 21, because the respective decay event can of course only be located in between the respective inner detector element 19 and the respective outer detector element and not, for instance, within a region 40. The probability functions 41 define portions d along the respective LOC 21, in which the respective decay event can be located. The TOF reconstruction preferentially uses a back projection algorithm, wherein during back projection values are projected only into the respective portions d weighted with the respective probability function 41. For more details regarding the TOF reconstruction reference is made to "Image Reconstruction from List-Mode Data in an Emission Tomography System Having Time-of-Flight Measurements" by D. L. Snyder DL and D.

G. Politte, WEE Transactions on Nuclear Science, 30:1843-1849 (1983), which is herewith incorporated by reference.

The PET/MR system 1 is preferentially adapted to be operated in full coincidence, i.e. any two detector elements from both, the outer ring 3 and the inner detector 6, are allowed to be paired for coincidence. The tailored, relatively narrow outer-inner timing window and also the outer-outer timing window can allow for a better rejection of random coincident detection events.

The PET/MR system 1 further comprises a display 16 for displaying the PET image and the MR image and an input unit 15 like a keyboard, a computer mouse, a touch pad, et cetera for inputting commands like a command for starting a PET data acquisition and/or and an MR data acquisition into the PET/MR system 1.

In another embodiment the PET data acquisition part and PET image reconstruction part of the PET/MR system 1 may form a separate PET system, without being integrated with an MR system. Moreover, in an embodiment the PET system may be integrated with another imaging modality not being an MR imaging modality like a CT imaging modality.

Figure 5:
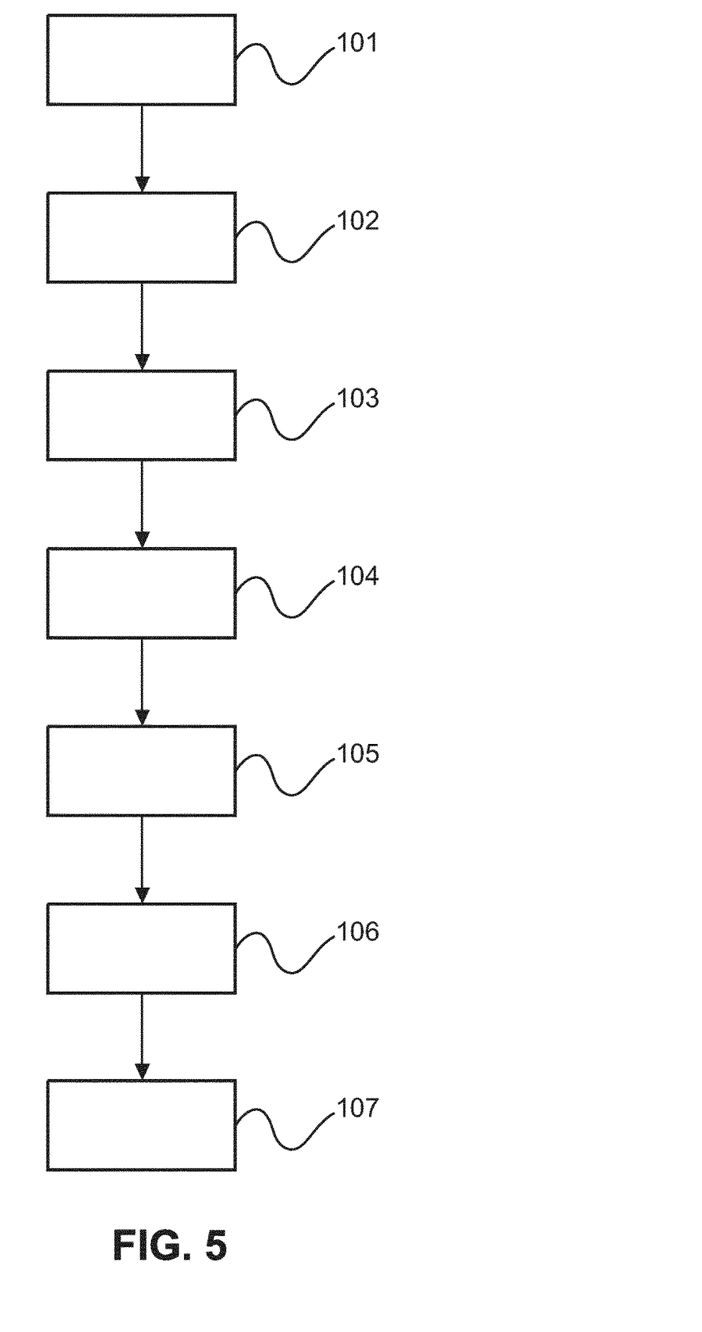
FIG. 5 shows a flowchart exemplarily illustrating an embodiment of a PET/MR method.

In the following an embodiment of a PET/MR method will be described with reference to a flowchart shown in FIG. 5.

In step 101 the MR data acquisition apparatus is used for generating MR data of the region of interest within the person, wherein the acquired MR data are used for reconstructing an MR image of the region of interest within the person. In step 102 the PET data acquisition apparatus is used for generating PET data. In particular, outer detection events being indicative of detected photons and detection times assigned to the outer detection events are generated by outer detector elements of the outer detector ring of the PET data acquisition apparatus. Moreover, inner detection events being indicative of detected photons and detection times assigned to the inner detection events are generated by the inner detector elements of the inner detector of the PET data acquisition apparatus.

In step 103 the position of the inner detector, in particular, the location and orientation relative to the outer detector ring, is provided by the position providing unit. Preferentially the inner detector is segmented in the reconstructed MR image for determining the position of the inner detector within the outer detector ring. In particular, by segmenting the inner detector in the reconstructed MR image, the position of the inner detector, especially of the inner detector elements, within an MR coordinate system defined by the MR system is known. Moreover, a transformation between the MR coordinate system and an outer PET detector coordinate system may have been defined in advance by calibration, which allows determining the position of the inner detector elements relative to the outer detector elements based on the reconstructed MR image and the transformation between the MR coordinate system and the outer PET detector ring coordinate system. In other embodiments the inner detector may be equipped with MR markers, especially with at least three MR markers, which are visible in the MR image and which can be used by the position providing unit for determining the position of the inner detector relative to the outer detector. In further embodiments the position of the inner detector can also be determined by using other position providing units like an electromagnetic or an optical shape sensing position providing unit, wherein based on the respective coordinates of the respective inner detector element and pre-determined spatial relations between the position providing unit and the outer detector ring the position of the respective inner detector element relative to the respective outer detector element can be determined.

In step 104 outer-inner timing windows and/or outer-outer timing windows are provided based on the position of the inner detector by the timing window determination unit. In step 105 outer-inner detection event pairs and outer-outer detection event pairs are generated based on the provided outer-inner timing windows and the provided outer-outer timing windows by the detection event pairs generation unit and in step 106 the PET image is reconstructed based on the generated outer-inner detection event pairs and outer-outer detection event pairs by the reconstruction unit. In step 107 the MR image and the PET image are shown on the display 16, for instance, as an overlay image or side by side. Steps 103 to 106 can be regarded as being steps of a reconstruction method for reconstructing a PET image.

For tailoring the outer-inner timing window the position, i.e. the location and orientation, of the inner detector relative to the outer detector ring is used. Although in the embodiment described above with reference to FIG. 1 an MR image has been used for determining the position of the inner detector, in another embodiment also another technique can be used for determining the position of the inner detector relative to the outer detector ring. For instance, the inner detector can comprise PET markers at known locations on and/or inside the inner detector, wherein the PET markers, which may also be regarded as being PET tracers forming fiduciary "beacons", emit pairs of photons, which can be detected by the outer detector ring for determining the position of the inner detector relative to the outer detector ring based on the detected photons. Also another tracking technique can be used for determining the position of the inner probe like the already above mentioned electromagnetic or optical shape sensing tracking techniques. The determination of the position of the inner detector may be performed at different points in time, in order to consider a possible motion of the inner detector relative to the outer detector ring, wherein the motion may be inner-person motion or a motion of the entire person.

Although in the embodiment described above with reference to FIG. 1 the inner detector is an endoprobe to be positioned within the person, in another embodiment the inner detector can also be another kind of detector, which is adapted to be arranged within the outer detector ring. For instance, the inner detector can be adapted to be arranged on an outer surface of the person. In an embodiment a tracked patch of digital PET detector elements is positioned on a part of the outer surface of the person, which is close to the region of interest, in particular, to the target organ. Also in this embodiment the inner detector may be tracked by using an imaging modality like the MR imaging modality, PET markers attached to the inner detector, electromagnetic tracking, optical shape sensing tracking, et cetera.

The inner detector may be adapted to be placed in the rectum or vagina, in order to obtain high quality images of the surrounding tissue. The above described systems may be adapted for determining, for instance, the extent of spread and local invasion of cancers of the prostate, the rectum, the anus, the cervix, et cetera.

Although in above described embodiments certain ways of determining the outer-outer timing window have been described, in other embodiments the outer-outer timing window can be provided in another way. For instance, a constant pre-determined outer-outer timing window can be provided for all outer-outer LOCs.

Although in above described embodiments the first detector is an outer detector ring and the second detector is an inner detector within the outer detector ring, in other embodiments the first and second detectors can also be other detectors. For instance, the first and second detectors can be two flat detectors like detectors of a positron emission mammography system, which may be arranged outside the person at opposite sides of the person.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the provision of the position of the inner detector, the provision of the timing windows, the generation of detection event pairs, the reconstruction of the images, et cetera performed by one or several units or devices can be performed by any other number of units or devices. For example, steps 103 to 106 can be performed by a single unit or by any other number of different units. These procedures and/or the control of the PET/MR system in accordance with the PET/MR method and/or the control of a PET system in accordance with a PET method and/or the control of a reconstruction apparatus for reconstructing a PET image in accordance with a reconstruction method for reconstructing the PET image can be implemented as program code means of a computer program and/or as dedicated hardware.

A standard PET coincidence logic, which may be implemented in hardware and which may operate on a fixed and preset firmware value for the timing window, can be augmented to allow for an LOC-dependent outer-inner timing window and/or outer-outer timing window. For instance, the preset value for the timing window can be left unchanged and the tailoring of the timing window, in order to obtain an LOC-dependent outer-inner timing window and/or outer-outer timing window, can be implemented in software and applied during reconstruction, i.e. during performing the above mentioned reconstruction method. In this way standard PET reconstruction can always be carried out and tailoring of the timing windows can be made optional. Since the tailoring of the timing windows leads to smaller timing windows, the standard hardware-based coincidence timing circuitry cannot discard events that the tailoring step would include. Timing information of the coincident photon pair is necessary for tailored windowing and is typically available in the PET data, which are generally list-mode data. The tailoring of the timing windows can therefore be performed as a separate additional data preparation step and added to the reconstruction pipeline.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a reconstruction apparatus for reconstructing a PET image. A first detector generates first detection events and detection times assigned to the first detection events and a second detector generates second detection events and detection times assigned to the second detection events. A timing window determination unit provides a first-second timing window by providing a first-second upper threshold based on the position of the second detector relative to the first detector and a detection event pairs generation unit generates first-second detection event pairs based on the provided first-second timing window, wherein the first-second detection event pairs are used for reconstructing the PET image. The provision of the first-second timing window depending on the position of the second detector can lead to an improved generation of first-second detection event pairs, which in turn can lead to an improved PET image.

The invention claimed is:

1. A reconstruction apparatus for reconstructing a PET image of an object, the reconstruction apparatus being adapted to reconstruct the PET image based on detection events and detection times assigned to the detection events generated by a PET data acquisition apparatus of a PET system, wherein the PET data acquisition apparatus comprises first detector elements configured to detect photons emitted by a radiation source located within the object and to generate first detection events indicative of the detected photons and detection times assigned to the first detection events, and second detector elements configured to detect photons emitted by the radiation source and generate second detection events indicative of the detected photons and detection times assigned to the second detection events, the reconstruction apparatus including a computer apparatus being configured to:
receive a position of the second detector relative to the first detector,
determine a first-second timing window including a first-second upper threshold based on the position of the second detector relative to the first detector,
generate first-second detection event pairs based on the provided first-second timing window, each first-second detection event pair including a first detection event and a second detection event, to which detection times have been assigned whose detection time difference is equal to or smaller than the first-second upper threshold, and
reconstruct the PET image based on the generated first-second detection event pairs.

2. The reconstruction apparatus as defined in claim 1, wherein the computer apparatus as further configured to determine a first-second lower threshold of the first-second timing window, wherein a difference between the detection times of each first-second event pair is equal to or larger than the first-second lower threshold.

3. The reconstruction apparatus as defined in claim 1, wherein the computer apparatus is further configured to:
receive an indication of a region of interest within the object which should be shown by the PET image, and,
determine the first-second timing window based on the region of interest.

4. The reconstruction apparatus as defined in claim 1, wherein the computer apparatus is configured to determine the first-second upper threshold for each first-second detection event pair based on a distance between a position of the respective first detector element and the position of the respective second detector element which detected the respective first and second detection events.

5. The reconstruction apparatus as defined in claim 1, wherein the computer apparatus is further configured to determine the first-second timing window based on borders of a region of interest along a line connecting a respective second detector element and a respective first detector element which detected the respective first and second detection events.

6. The reconstruction apparatus as defined in claim 1, wherein the computer apparatus is configured to determine the position of the second detector based on an image received from a further imaging system integrated and which shows the second detector.

7. The reconstruction apparatus as defined in claim 1, wherein the computer apparatus is further configured to:
provide a first-first timing window including a first-first upper threshold,
generate first-first detection event pairs based on the first-first timing window, wherein a first-first detection event pair comprises first detection events, to which detection times have been assigned whose difference is equal to or smaller than the first-first upper threshold, and
reconstruct the PET image based on the generated first-second detection event pairs and the first-first detection event pairs.

8. A reconstruction method for reconstructing a PET image of an object, the reconstruction method being adapted to reconstruct the PET image based on detection events and detection times assigned to the detection events generated by a PET data acquisition apparatus of a PET system, wherein the PET data acquisition apparatus includes a first detector with first detector elements for detecting photons emitted by a radiation source located within the object and for generating first detection events indicative of the detected photons and detection times assigned to the first detection events and a second detector with second detector elements for detecting photons emitted by the radiation source and for generating second detection events indicative of the detected photons and detection times assigned to the second detection events, the reconstruction method comprising:
determining a position of the second detector relative to the first detector,
determining a first-second timing window including a first-second upper threshold based on the position of the second detector relative to the first detector,
generating first-second detection event pairs based on the first-second timing window, each first-second detection event pair including a second detection event and a first detection event, to which detection times have been assigned, a difference in a time between the first and second detection times being equal to or smaller than the first-second upper threshold, and
reconstructing the PET image based on the generated first-second detection event pairs with a processor.

9. A PET method for generating a PET image of an object, the PET method comprising:
detecting photons emitted by a radiation source located within the object and generating first detection events indicative of the detected photons and detection times assigned to the first detection events by first detector elements of a first detector,
detecting photons emitted by the radiation source located within the object and generating second detection events indicative of the detected photons and detection times assigned to the second detection events by second detector elements of a second detector,
reconstructing the PET image with the method defined in claim 8.

10. A non-transitory computer-readable medium carrying program code for causing a PET system including one or more computers to carry out the steps of the PET method as defined in claim 9.

11. A non-transitory computer-readable medium carrying program code for causing a processor to carry out the method as defined in claim 8.

12. A reconstruction apparatus for reconstructing positron emission tomography (PET) images, the apparatus comprising one or more processors configured to:
receive first detection events from detector elements of a first detector, each first detection event having an associated detection time,
receive second detection events from detector elements of a second detector, each second detection event having an associated detection time,
determining a timing window corresponding to each pair of first and second detection events based on a relative location of the detector elements which generated the pair of the first and second detection events, and
reconstruct the pairs of first and second detection events whose differences in the associated times are within the corresponding timing window into the PET image.

13. A PET system for generating a PET image of an object, the PET system comprising:
a first detector with first detector elements for detecting photons emitted by a radiation source located within the object and for generating first detection events indicative of the detected photons and detection times assigned to the first detection events,
a second detector with second detector elements for detecting photons emitted by the radiation source and for generating second detection events indicative of the detected photons and detection times assigned to the second detection events,
a reconstruction apparatus for reconstructing a PET image as defined in claim 12.

14. The PET system as defined in claim 13, wherein the first detector is an outer detector ring and the first detector elements are outer detector elements, wherein the outer detector ring surrounds an examination region,
the second detector is an inner detector and the second detector elements are inner detector elements, wherein the inner detector is adapted for detecting the photons inside the outer detector ring.

15. The PET system as defined in claim 13, wherein the second detector is adapted for being introduced into the object for detecting the photons inside the object.

16. The reconstruction apparatus as defined in claim 12, wherein the timing window includes an upper threshold.

* * * * *